United States Patent
Wang et al.

(10) Patent No.: US 12,426,985 B1
(45) Date of Patent: Sep. 30, 2025

(54) DISPLAY DEVICE AND SYSTEM FOR THREE-DIMENSIONAL VIRTUAL MODEL OF LIVING ORGANISM, AND MIXED REALITY DEVICE

(71) Applicant: Xiangya Hospital of Central South University, Changsha (CN)

(72) Inventors: Chenggong Wang, Changsha (CN); Xi Li, Changsha (CN); Zhen Yin, Changsha (CN)

(73) Assignee: Xiangya Hospital of Central South University, Changsha (CN)

( * ) Notice: Subject to any disclaimer, the term of this patent is extended or adjusted under 35 U.S.C. 154(b) by 0 days.

(21) Appl. No.: 19/171,389

(22) Filed: Apr. 7, 2025

(30) Foreign Application Priority Data

Nov. 21, 2024 (CN) .......................... 202411667982.X

(51) Int. Cl.
    *A61B 90/00* (2016.01)
    *A61B 34/10* (2016.01)
    (Continued)

(52) U.S. Cl.
    CPC .............. *A61B 90/37* (2016.02); *A61B 34/10* (2016.02); *G06T 7/344* (2017.01); *G06T 7/75* (2017.01); *G06T 17/00* (2013.01); *G06T 19/006* (2013.01); *A61B 2034/105* (2016.02); *A61B 2034/107* (2016.02); *A61B 2090/365* (2016.02);
    (Continued)

(58) Field of Classification Search
CPC ... A61B 90/37; A61B 34/10; A61B 2034/105; A61B 2034/107; A61B 2090/365; G06T 7/344; G06T 7/75; G06T 17/00; G06T 19/006; G06T 2200/04; G06T 2207/10081; G06T 2207/10116; G06T 2207/20081; G06T 2207/30004; G06T 2207/30196; G06T 2207/30204; G06T 2210/41

See application file for complete search history.

(56) References Cited

U.S. PATENT DOCUMENTS

| | | | |
|---|---|---|---|
| 2016/0239631 A1* | 8/2016 | Wu | G16Z 99/00 |
| 2019/0159743 A1* | 5/2019 | Ma | A61B 6/466 |

(Continued)

FOREIGN PATENT DOCUMENTS

| | | |
|---|---|---|
| CN | 106890025 A | 6/2017 |
| CN | 109272472 A | 1/2019 |

(Continued)

*Primary Examiner* — Maurice L. McDowell, Jr.
(74) *Attorney, Agent, or Firm* — IPRTOP LLC

(57) ABSTRACT

The present disclosure provides a display device and system for a three-dimensional virtual model of a living organism, as well as a mixed reality device. The display device comprises a construction module, configured to construct a first virtual model comprising body surface features and internal features of a living organism based on two-dimensional scanning data and image data of the living organism collected during surgery; a calibration module, configured to calibrate the first virtual model by using a second virtual model of the living organism to obtain a calibrated first virtual model; a display module, configured to determine a pose of the calibrated first virtual model in a real world scenario based on the image data of a body surface marker to display the calibrated first virtual model and the real world scenario through a mixed reality device.

14 Claims, 6 Drawing Sheets

(51) Int. Cl.
*G06T 7/33* (2017.01)
*G06T 7/73* (2017.01)
*G06T 17/00* (2006.01)
*G06T 19/00* (2011.01)

(52) U.S. Cl.
CPC ............ *G06T 2200/04* (2013.01); *G06T 2207/10081* (2013.01); *G06T 2207/10116* (2013.01); *G06T 2207/20081* (2013.01); *G06T 2207/30004* (2013.01); *G06T 2207/30196* (2013.01); *G06T 2207/30204* (2013.01); *G06T 2210/41* (2013.01)

(56) References Cited

U.S. PATENT DOCUMENTS

| | | | |
|---|---|---|---|
| 2021/0065451 A1 | 3/2021 | Tseng et al. | |
| 2022/0183760 A1* | 6/2022 | Fouts | ............ G16H 20/40 |
| 2024/0065774 A1* | 2/2024 | Chaoui | ............ A61B 34/20 |
| 2024/0315776 A1 | 9/2024 | Zhang et al. | |
| 2025/0025128 A1* | 1/2025 | Chaoui | ............ A61B 8/42 |

FOREIGN PATENT DOCUMENTS

| | | |
|---|---|---|
| CN | 111798451 A | 10/2020 |
| CN | 112598649 A | 4/2021 |
| CN | 113256814 A | 8/2021 |
| CN | 114366330 A | 4/2022 |
| CN | 114842004 A | 8/2022 |
| CN | 114983567 A | 9/2022 |
| CN | 117765209 A | 3/2024 |
| CN | 118660677 A | 9/2024 |
| CN | 118840379 A | 10/2024 |
| KR | 20180099039 A | 9/2018 |

\* cited by examiner

DISPLAY DEVICE AND SYSTEM FOR THREE-DIMENSIONAL VIRTUAL MODEL OF LIVING ORGANISM, AND MIXED REALITY DEVICE

FIELD OF TECHNOLOGY

The present disclosure relates to the technical field of medical data processing, and in particular to a display device and system for a three-dimensional virtual model of a living organism, and a mixed reality device.

BACKGROUND

Mixed Reality (MR) technology involves merging of computer-generated images and the real world, allowing virtual images to be displayed in a physical environment. This enables the human eye to see virtual objects in the real world. One of the most well-known MR devices is the optical see-through head-mounted display, HoloLens, which provides real-time spatial positioning using simultaneous localization and mapping technology and multiple interaction functions such as voice commands and gestures, providing users with an immersive experience.

With the development of Mixed Reality (MR) technology, researchers have explored its applications in surgical navigation and telesurgery. Currently, preoperative scanning data, such as computed tomography data (CT data), is employed to generate a three-dimensional virtual model of the internal structure of the patient. During surgery, the corresponding physical anatomical entity (such as organs or bones) is identified to align with the three-dimensional virtual model. By using the MR device worn by the surgeon, the three-dimensional virtual model and the corresponding physical anatomical entity are integrated and simultaneously displayed within the surgeon's field of view, providing the surgeon with an "X-ray vision". Currently, infrared reflective markers, which can be tracked by optical tracking devices, have to be manually fixed onto the physical anatomical entity (such as bones) corresponding to the three-dimensional virtual model to determine their pose, thereby achieving the fusion display of the three-dimensional virtual model and the corresponding physical anatomical entity.

However, through long-term clinical practice, doctors have found that this approach fails to achieve precise alignment and fusion display between virtual images and the lesion region of the patient. The alignment relies heavily on manual adjustments of the virtual image poses, is highly dependent on network signal quality, and takes a long time, therefore, most critically, precise and real-time display cannot be achieved. Additionally, directly fixing infrared reflective markers onto the physical anatomical entity requires invasive procedures (such as cutting the skin to expose the bones or organs). However, orthopedic surgeries are complex and delicate, demanding precise identification and localization of tissue structures such as joints, bones, ligaments, muscles, and nerves. Factors such as operation duration, blood loss, wound area, and patient pain also have to be taken into consideration. Due to the small surgical visual field and limited operating space, invasive procedures pose significant challenges to the surgeon. Furthermore, the manual placement of the infrared reflective markers depends on the subjective visual perception of the operator (surgeon or nurse), which is not only time-consuming but also often fails to achieve the precise alignment between the three-dimensional virtual model and the corresponding physical anatomical entity.

SUMMARY

The present disclosure provides a display device and system for a three-dimensional virtual model of a living organism, as well as a mixed reality device, which avoids invasive procedures caused by the use of infrared reflective markers to display the three-dimensional virtual model and achieves precise alignment between the three-dimensional virtual model and the corresponding physical anatomical entity.

The first aspect of the present disclosure provides a display device for a three-dimensional virtual model of a living organism, comprising a construction module, configured to construct a first virtual model comprising body surface features and internal features of a living organism based on two-dimensional scanning data and image data of the living organism collected during surgery; wherein the two-dimensional scanning data of the living organism includes scanning data of a body surface marker and internal tissue of a target area of the living organism, and the image data of the living organism includes image data of a body surface marker and body surface of the target area of the living organism; a calibration module, configured to calibrate the first virtual model by using a second virtual model of the living organism to obtain a calibrated first virtual model; wherein the second virtual model is pre-constructed based on preoperative CT data of the living organism, and the second virtual model includes the internal features of the living organism; a display module, configured to determine a pose of the calibrated first virtual model in a real world scenario based on the image data of the body surface marker to display the calibrated first virtual model and the real world scenario through a mixed reality device.

The second aspect of the present disclosure provides a display system for a three-dimensional virtual model of a living organism, comprising: a computer device, configured to construct a first virtual model comprising body surface features and internal features of the living organism based on the two-dimensional scanning data and image data of the living organism collected during surgery; and to calibrate the first virtual model by using a second virtual model of the living organism to obtain a calibrated first virtual model; wherein the two-dimensional scanning data comprises scanning data of a body surface marker and internal tissue of a target area of the living organism, and the image data of the living organism comprises image data of a body surface marker and body surface of the target area of the living organism; wherein the second virtual model is pre-constructed based on preoperative CT data of the living organism, and the second virtual model includes internal features of the living organism; a mixed reality device, connected to the computer device, configured to determine a pose of the calibrated first virtual model in a real world scenario based on the image data of the body surface marker to display the calibrated first virtual model and the real world scenario through the mixed reality device.

The third aspect of the present disclosure provides a mixed reality device, comprising: a sensor device, configured to collect image data of a living organism; a storage device, configured to store at least one program; a display device, configured to fuse a virtual model with a real world scenario for display; a processing device, connected to the sensor device, storage device, and display device, configured to invoke and execute the at least one program from the storage device to achieve the following: constructing a first virtual model comprising body surface features and internal features of the living organism based on two-dimensional scanning data and image data of the living organism collected during surgery; wherein the two-dimensional scanning data of the living organism comprises scanning data of a body surface marker and internal tissue of a target area of the living organism, and the image data of the living organism comprises image data of a body surface marker and body surface of the target area of the living organism; calibrating the first virtual model by using a second virtual model of the living organism to obtain a calibrated first virtual model; wherein the second virtual model is pre-constructed based on preoperative CT data of the living organism, and the second virtual model comprises internal features of the living organism; determining a pose of the calibrated first virtual model in the real world scenario based on the image data of the body surface marker to display the calibrated first virtual model and the real world scenario through the mixed reality device.

In summary, the present disclosure provides a display device and system for a three-dimensional virtual model of a living organism, as well as a mixed reality device. By constructing a first virtual model based on the two-dimensional scanning data and the image data of the living organism collected during intraoperative period, the display device and system ensure that the body surface features and internal features of the first virtual model correspond to the actual state/pose of the target area of the living organism during intraoperative period. Furthermore, by calibrating the first virtual model with the second virtual model constructed preoperatively, the dimensions of the internal features in the calibrated first virtual model match the actual dimensions of the internal features of the living organism. Generally speaking, through the body surface marker attached to the body surface, the calibrated first virtual model can be fused with the real world scenario for display without the need for invasive procedures, and precise alignment between the three-dimensional virtual model and the corresponding physical anatomical entity is realized, thereby facilitating clinical surgical applications.

BRIEF DESCRIPTION OF THE DRAWINGS

By referring to the exemplary embodiments and accompanying drawings described in detail below, the features and advantages of the present disclosure can be better understood. A brief description of the drawings is as follows.

DETAILED DESCRIPTION

Figure 1:
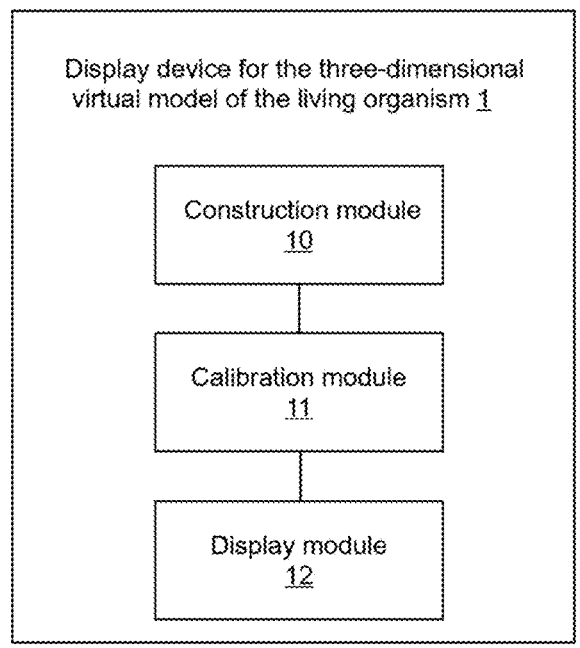
FIG. 1 shows a schematic structural diagram of a display device for a three-dimensional virtual model of the living organism in one embodiment of the present disclosure.

The embodiments of the present disclosure will be described below. Those skilled in the art may easily understand the advantages and effects of the present disclosure according to the contents disclosed in this specification. In the following description, some embodiments can be better understood with reference to the accompanying drawings. It should be understood that other embodiments without accompanying drawings may also be included, and that changes in specific steps, modules or units, electrical configurations, and operations can be made without departing from the spirit and scope of the present disclosure. The following detailed description should not be considered limiting, and the scope of the embodiments of the present disclosure is limited only by the claims of the present disclosure. The terms used herein are for describing particular embodiments only, and are not intended to limit the present disclosure.

Although the terms "first", or "second", etc. are used herein to describe various elements in some embodiments, these elements are not limited by these terms. These terms are only used to distinguish one object from another and are not intended to limit the order, timing, priority, or importance of multiple objects. For example, the first virtual model may be referred to as the second virtual model, and similarly, the second virtual model may be referred to as the first virtual model, without departing from the scope of the various described embodiments. Both the first virtual model and the second virtual model are virtual models, however, unless the context clearly indicates otherwise, they are not the same virtual model.

In addition, as used herein, the singular forms "a", "an" and "the" are intended to include the plural forms as well, unless the context clearly indicates otherwise. It should be further understood that the terms "comprise", and "include" indicate that there are the described features, steps, operations, elements, components, items, categories, and/or groups, but the existence, presence, or addition of one or more other features, steps, operations, elements, components, items, categories, and/or groups are not excluded. For example, a process, method, system, product, or device that includes a series of steps or units is not limited to those steps or units explicitly listed, and may also include other steps or units that are inherent to the processes, methods, products, or devices, or that are not explicitly listed. Additionally, the term "and/or" used in the following text may describe the relationship between objects, indicating that there may be three possible relationships. For example, "A and/or B" can represent the following: A alone, both A and B together, and B alone. Additionally, the character "/" generally represents an "and/or" relationship between objects, unless otherwise specified. Moreover, in the embodiments of the present disclosure, the term "multiple" refers to two or more.

The following is an explanation of some terms or terminology used in the embodiments of the present disclosure, which are also considered a part of the present disclosure. Those skilled in the art would understand that, unless otherwise defined, all terms including the technical terms and scientific terms used herein have the same meaning as commonly understood by those skilled in the art to which the present disclosure relates. It should also be understood that terms, such as those defined in common dictionaries, should be understood to have meanings consistent with their context in the prior art, unless specifically defined otherwise, they should not be interpreted with idealized or overly formal meanings.

As used herein, the term "computer device" refers to any programmable computer system, whether currently known or to be developed in the future. In preferred embodiments, the computer will be coupled to a network. The computer system may be configured with a processor capable of executing software instructions to perform the processes described herein.

As used herein, the term "module" is intended to refer to computer-related entities, whether the computer-related entities are hardware, a combination of hardware and software, software, or software in execution. For example, a module can be, but is not limited to, a process running on a processor, a processor, an object, an executable file, a running thread, a program, and/or a computer. In the embodiment, both an application running on a server and the server itself can be considered modules. One or more modules may reside within a process and/or an executing thread, and the module may be localized on a single computer and/or distributed across two or more computers.

As used herein, the term "pose" includes both position and orientation. The position can be represented by numerical values along the three axes (x, y, z) of a three-dimensional space coordinate system. For example, the position of the calibrated first virtual model in the real world scenario can be represented by numerical values along the three coordinate axes of a world coordinate system. The orientation can be represented by three rotation angles (pitch, yaw, roll) corresponding to the three axes (x, y, z) of the three-dimensional space coordinate system. For example, the orientation of the calibrated first virtual model in the real world scenario can be represented by the rotation angles (pitch, yaw, roll) corresponding to rotations of the calibrated first virtual model around the three axes (x, y, z) of the world coordinate system.

The real world scenario refers to the physical world that people can perceive and/or interact with without the aid of electronic systems. The real world scenario, such as a hospital operating room, includes physical items, physical objects, or real objects, such as living organisms and surgical instruments. People are able to directly sense and/or interact with the real world scenario through sensory modalities such as vision, touch, hearing, taste, and smell.

A virtual reality (VR) environment refers to a simulated environment that is designed to provide completely computer-generated sensory inputs. A virtual reality (VR) environment includes multiple virtual objects with which a person can sense and/or interact. For example, virtual objects include computer-generated images of hospital beds, surgical instruments, and human avatars.

Compared to a virtual reality (VR) environment which is designed to provide completely computer-generated sensory inputs, a mixed reality (MR) environment refers to a simulated environment that includes not only computer-generated sensory inputs (e.g., virtual objects) but also sensory inputs from real world scenario or their representations. On the reality-virtuality continuum, an MR environment is any state between a fully physical environment at one end and a virtual reality (VR) environment at the other end, excluding these two endpoints.

A mixed reality (MR) device refers to a device that can fuse and display virtual objects (such as a calibrated virtual model) with the real world scenario. Furthermore, users can interact with the virtual objects. For example, the MR device may be a head-mounted mixed reality device (such as mixed reality glasses).

Given the background described, existing technology for displaying three-dimensional virtual models based on infrared reflective markers results in invasive procedures and fails to achieve precise alignment between the virtual model and the corresponding physical anatomical entity. For example, the current method for aligning virtual images with lesion regions based on HoloLens involves fixing a rigid body positioning target with infrared reflective markers to surgical tools or bony landmarks. This method also requires an external optical tracking system to track the pose of the reflective infrared markers on the positioning target within the coordinate system. However, this process heavily relies on manual adjustments of the positioning target for alignment, depending on the surgeon's subjective visual perception, which is not only time-consuming, but also fails to achieve precise alignment. Furthermore, when the spatial position of the positioning target changes, the optical tracking system needs to recalculate the pose information. In real surgical scenarios, the patient's limbs often cannot remain completely stationary, therefore, the surgeon has to perform continuous intraoperative manipulation, making real-time tracking difficult. Additionally, during the alignment between the three-dimensional virtual model and the corresponding physical anatomical entity, issues such as optical path occlusion or sudden displacement of the positioning target can easily lead to image jitter, which may adversely affect the surgeon's operational precision during surgery.

Furthermore, in the current fusion display of the three-dimensional virtual models and the corresponding physical anatomical entity, apart from the display device like Hololens glasses, an optical tracking system is also required. This optical tracking system occupies considerable space in the operating room and has a limited optical signal transmission range of only 2 meters. When this range is exceeded, image loss may occur. The display device is highly dependent on the quality of the network signal. When the signal is weak, image jitter, unclear virtual images, or the virtual image loss may occur, leading to issues such as imprecise alignment and delays in alignment, which affects the progress of the surgery. In addition to the aforementioned optical tracking system, the rigid body positioning target, which is equipped with infrared reflective markers, is also required. As the infrared reflective markers cannot be reused, new positioning targets must be purchased for each surgical procedure, consequently increasing the cost of the surgery.

Furthermore, since the three-dimensional virtual model is preoperatively generated, directly displaying the preoperative three-dimensional virtual model during surgery may result in inaccurate alignment between the virtual model and the corresponding physical anatomical entity due to differences in the pose of the body, restricting widespread clinical application. For example, a preoperative three-dimensional virtual model of a human foot created in a flat position is generated. If during surgery, the patient's foot is bent, the positions of bones inside the foot will change accordingly, additionally, the relative positional relationship between the skin and bones of the foot may also change, causing a mismatch between the preoperative foot model and the actual foot during surgery. As a result, this makes it difficult to achieve precise alignment and limits the clinical application of the preoperative model.

The present disclosure will be described in detail by using the drawings and embodiments below. The technical solutions in the embodiments of the present disclosure will be described clearly and completely below. The described embodiments are only a part of the embodiments of the present disclosure. Based on the embodiments of the present disclosure, all other embodiments and their technical effects that a person skilled in the art could obtain without creative efforts still fall within the scope of the present disclosure. The phrases "one embodiment", "an embodiment", or similar expressions used throughout this specification mean that the specific features, structures, or characteristics described within the embodiment are included in at least one embodiment of the present disclosure. Therefore, in this specification, the phrases like "in one embodiment", "in an embodiment", or similar expressions may (but not necessarily) refer to the same embodiment.

The present disclosure discloses a display device for a three-dimensional virtual model of a living organism. The display device generates a first virtual model using the two-dimensional scanning data and the image data of the living organism collected intraoperatively. This ensures that the body surface features and internal features of the first virtual model correspond to the actual pose/state of the target area of the living organism during intraoperative period. Furthermore, by calibrating the first virtual model with the second virtual model generated preoperatively, the dimensions of the internal features of the calibrated first virtual model match the actual dimensions of the internal features of the living organism. Additionally, the body surface marker attached to the body surface enables the calibrated first virtual model to be fused with the real world scenario for display without the need for invasive procedures, achieving precise alignment between the three-dimensional virtual model and the corresponding physical anatomical entity, thereby facilitating clinical surgical applications.

In some embodiments, the display device for the three-dimensional virtual model of the living organism can be fully localized within the mixed reality device, or distributed across the mixed reality device and one or more computer devices that are in communication/network connection with the mixed reality device. The configuration of the display device for the three-dimensional virtual model of the living organism is not restricted in the present disclosure, as long as it is capable of generating the first virtual model through mutual communication, calibrating the first virtual model, and displaying the calibrated first virtual model and the real world scenario through the mixed reality device.

Please refer to FIG. 1, which shows a schematic structural diagram of the display device for the three-dimensional virtual model of the living organism in one embodiment of the present disclosure. As shown in FIG. 1, the display device for the three-dimensional virtual model of the living organism 1 comprises a construction module 10, a calibration module 11, and a display module 12.

The construction module 10, calibration module 11, and display module 12 can be implemented by the software running on different types of processors. For example, the executable module may include one or more physical or logical blocks of computer instructions, which are organized as objects, programs, or functions. However, the executable files of the module do not have to be physically located together; they may include commands stored in different locations. When these commands are logically connected, they collectively constitute the module and achieve the specified objectives of the module.

Certainly, the executable module can consist of one or more instructions and can even be distributed across several different code segments different programs, and multiple storage devices. Similarly, computational data can be identified and illustrated within the module, and such data can be embodied in any suitable form and organized in any appropriate type of data structure. The computational data can be collected as a single data set or distributed across different locations (including different storage devices), and may exist at least partially as electrical signals within a system or network. When a module or a part of a module is implemented in the software, the software is stored on one or more computer-readable media.

The construction module 10 is configured to construct a first virtual model comprising body surface features and internal features of the living organism based on the two-dimensional scanning data and the image data of the living organism collected intraoperatively. Specifically, the construction module 10 acquires the two-dimensional scanning data and the image data of the living organism collected intraoperatively, and constructs a first virtual model based on the two-dimensional scanning data and the image data of the living organism collected intraoperatively. The living organism refers to either a human body or an animal body. In the following embodiments, the left foot of a human body is used as an example for illustration. The terms "during surgery", "intraoperatively", and "intraoperative period" refer to the process in which the living organism is positioned on a supporting platform in a hospital operating room, either preparing for or performing surgery. The supporting platform can be, for example, a surgical table, hospital bed, examination table, etc.

Figure 2A:
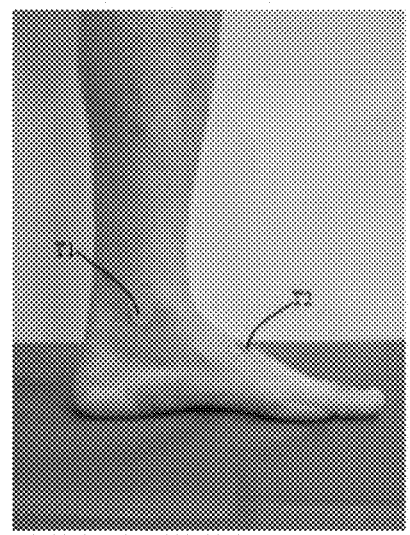
FIG. 2a shows a side view of a human left foot attached with a body surface marker in one embodiment of the present disclosure.
Figure 2B:
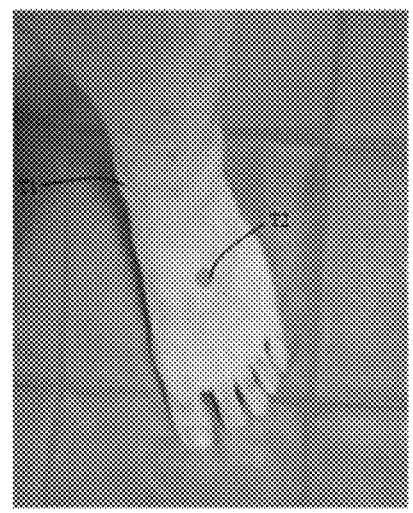
FIG. 2b shows a top view of the human left foot attached with the body surface marker in one embodiment of the present disclosure.

Before collecting the two-dimensional scanning data and the image data intraoperatively, at least one body surface marker is attached to the body surface (the surface of the body) of the target area of the living organism. The target area includes both the internal surgical site and the body surface corresponding to the internal surgical site. For example, if the surgical site is one or more bones in the left foot of the human body, the corresponding target area can be the entire left foot. Please refer to FIGS. 2*a* and 2*b*. FIG. 2*a* shows a side view of the human left foot attached with the body surface marker in an embodiment of the present disclosure. FIG. 2*b* shows a top view of the human left foot attached with the body surface marker in an embodiment of the present disclosure. As shown in the figures, before collecting the two-dimensional scanning data and the image data intraoperatively, the body surface markers T1 and T2 are respectively attached on the body surface corresponding to the ankle and the dorsum of the left foot of the patient.

In one embodiment, the body surface marker includes a physical object that can be detected by a transmissive scanning device. The physical object can be affixed to the body surface of the target area or placed on the body surface of the target area through methods such as wearing. The number of physical objects can be one or multiple. The physical object can be spherical, linear, and/or planar. For example, the physical object may be a QR code sticker. Alternatively, the physical object may be a circular patch shown in FIGS. 2*a* and 2*b*. In another embodiment, the body surface marker may be a pattern marker that can be detected by a transmissive scanning device. Specifically, the user (e.g., the doctor) can draw a pattern marker on the body surface of the target area using a material that can be detected by a transmissive scanning device. The pattern marker may include dots, lines, and/or planes. The material used for drawing the pattern marker is related to the type of the transmissive scanning device. For example, if the transmissive scanning device is an X-ray device, the material for drawing the pattern marker can be a fluorescent powder used for X-ray imaging. It should be noted that the present disclosure does not impose limitations on the shape or structure of the body surface marker and the material used for drawing the pattern marker, as long as the body surface marker is distinguishable from human tissues or bones, etc., and detectable by the transmissive scanning device.

In one embodiment, after the configuration of the body surface marker is completed, the user (e.g., the doctor or nurse) uses a transmissive scanning device to collect two-dimensional scanning data of the living organism during surgery. Specifically, the user uses the transmissive scanning device to visualize the target area of the living organism and collect the two-dimensional scanning data during surgery. The two-dimensional scanning data is then transmitted or imported into the mixed reality device or the computer device with the construction module, so that the construction module can acquire the collected two-dimensional scanning data. In this embodiment, the transmissive scanning device is an X-ray transmissive scanning device. For example, the X-ray transmissive scanning device is a C-arm X-ray machine. The X-ray transmissive scanning device when being used as the transmissive scanning device can reduce the radiation exposure of the living organism during surgery.

Figure 3A:
FIG. 3a shows a side-view X-ray image of the human left foot in one embodiment of the present disclosure.
Figure 3B:
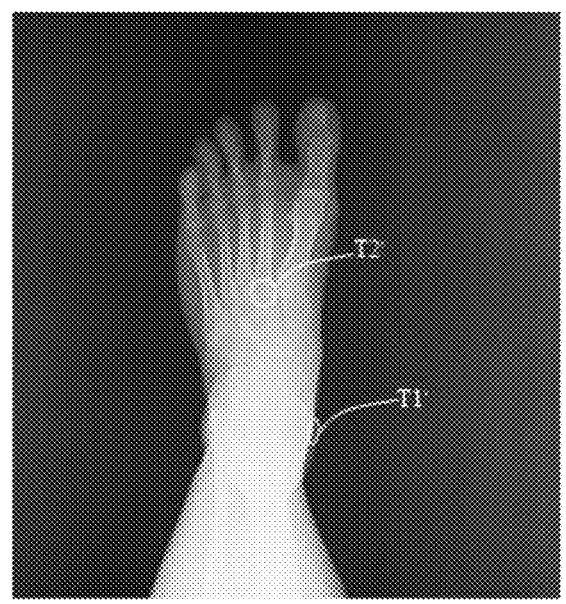
FIG. 3b shows a top-view X-ray image of the human left foot in one embodiment of the present disclosure.

In one embodiment, the collected two-dimensional scanning data of the living organism includes the scanning data of the body surface marker and the internal tissue of the target area of the living organism. In one embodiment, the transmissive scanning device is an X-ray transmissive scanning device, and the collected two-dimensional scanning data of the living organism includes the anteroposterior X-ray data and/or lateral X-ray data of the target area of the living organism. Please refer to FIGS. 3*a* and 3*b*. FIG. 3*a* shows a schematic diagram of the lateral X-ray image of the human left foot in one embodiment of the present disclosure, and FIG. 3*b* shows a schematic diagram of the anteroposterior X-ray image of the human left foot in one embodiment of the present disclosure. As shown in the figures, after the human left foot is scanned using the X-ray transmissive scanning device, the lateral X-ray image and the anteroposterior X-ray image show not only the image features (T1', T2') of the body surface marker of the target area of the human left foot, but also the image features of the internal tissue of the human left foot. These image features serve as the scanning data for subsequent construction of the first virtual model, which includes both the body surface features and internal features of the human left foot.

In one embodiment, the two-dimensional scanning data of the living organism includes coordinate data (pixel coordinates) of the body surface marker and the internal tissue of the target area of the living organism, as well as the light intensity data (pixel values) corresponding to the coordinate data. For example, the two-dimensional scanning data of the left foot includes the coordinate data of the body surface marker, the internal tissue (bones, organs, etc.), and the body surface of the left foot, as well as the light intensity data corresponding to the coordinate data. It should be noted that the internal bones and internal organs absorb X-rays to different extents, and as a result, the light intensity data corresponding to the coordinate data of the internal bones and internal organs also differs from each other. Therefore, the body surface marker, the internal tissue (e.g., bones, organs, etc.), and the body surface can be distinguished based on the light intensity data.

In one embodiment, the image data of the living organism is collected in real time by the mixed reality device during surgery. For example, it is acquired in real time by the sensor device in the mixed reality device, which will be described in detail later. Alternatively, the image data of the living organism can also be acquired in real time by a camera in the hospital surgical room. The camera transmits the real-time image data to the mixed reality device or the computer device with the construction module. In a specific embodiment, the user (e.g., the doctor) wears the mixed reality device during surgery, and the sensor device of the mixed reality device acquires the image data of the living organism in real time. In the following embodiments, the image data of the living organism is acquired in real-time by the mixed reality device during surgery. It should be noted that if the target area of the living organism is chosen during surgery, the target area will not change, and the image data of the living organism may also be acquired in a single time during surgery by the mixed reality device.

In one embodiment, the image data of the living organism includes the image data of the body surface and the body surface marker of the target area of the living organism. Specifically, the image data of the living organism includes the coordinate data (pixel coordinates) of the body surface and the body surface marker of the target area, as well as the light intensity data (pixel values) corresponding to the coordinate data. The light intensity data can include single-channel light intensity data or multi-channel light intensity data. In other words, the image data of the living organism can be color image data or black-and-white image data. It should be noted that since the image data is not scanning data obtained through the transmissive scanning device, the image data does not include those of the internal tissue of the target area.

Figure 4:
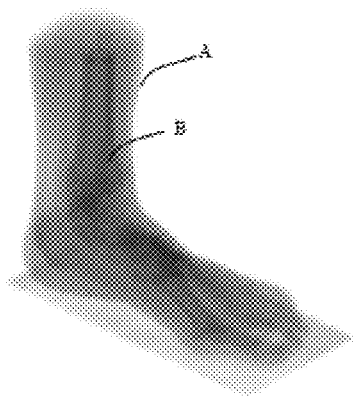
FIG. 4 shows a schematic diagram of a first virtual model in one embodiment of the present disclosure.

After the construction module 10 acquires the two-dimensional scanning data and the image data of the living organism collected during surgery, it constructs the first virtual model that includes both the body surface features and internal features of the living organism, based on the two-dimensional scanning data and the image data. The body surface features of the living organism include the three-dimensional features of the external contour of the target area, and may further include the three-dimensional features of the external tissue of the target area. For example, when the target area is the foot, the body surface features of the foot include the three-dimensional features of the external contour of the foot, as well as the three-dimensional features of the external tissue of the foot, such as the toenails. The internal features include the three-dimensional features of the internal tissue of the target area, such as internal bones and internal organs. For example, when the target area is the foot, the internal features include the three-dimensional features of multiple bones in the foot. Furthermore, in one embodiment, the first virtual model may also include the three-dimensional features of the body surface marker. For example, referring to FIG. 4, which shows a schematic diagram of the first virtual model in one embodiment. As shown in the figure, the first virtual model of the foot includes the body surface feature A and the internal feature B of the foot. The body surface feature A includes the three-dimensional feature of the external contour of the foot, and the internal feature B includes the three-dimensional feature of the bones of the foot. Thus, the body surface features and internal features of the first virtual model, which are constructed based on the two-dimensional scanning data and the image data of the living organism collected during surgery, align with the actual state or actual pose of the target area during surgery.

Furthermore, in one embodiment, the first virtual model may also include the three-dimensional features of the body surface marker. It should be noted that the three-dimensional features of the body surface marker may be included in the first virtual model or not included in the first virtual model. In an embodiment, when the three-dimensional features of the body surface marker are not included in the first virtual model, the construction module 10 only provides the pose of the body surface marker in the first virtual model to reduce the data size of the first virtual model.

In one embodiment, the transparency of the first virtual model is set to 0.5. This can prevent the first virtual model from completely obscuring the real world scenario, thereby improving the safety of the surgery.

In one embodiment, the two-dimensional scanning data and the image data of the living organism is directly input into a pre-trained model construction network in the construction module 10 to obtain the first virtual model. The model construction network can be a three-dimensional Recurrent Reconstruction Neural Network (3D-R2N2), Convolutional Neural Network, Deep Neural Network, or Generative Adversarial Network, etc. The training method for the model construction network will be described in detail later.

In another embodiment, before constructing the first virtual model, the construction module 10 further performs feature point detection and matching on the collected two-dimensional scanning data and image data. This is to determine the first body surface feature point and the second body surface feature point that represent the same body surface feature point in the two-dimensional scanning data and image data, as well as to identify the internal feature point in the two-dimensional scanning data. In this embodiment, the construction module 10 can construct the first virtual model, which includes both the body surface features and internal features of the living organism, based on the coordinate data of the first body surface feature point and internal feature point in the two-dimensional scanning data, as well as the coordinate data of the second body surface feature point in the image data of the living organism. For example, the two-dimensional scanning data and the corresponding coordinate data of the first body surface feature point and internal feature point, as well as the image data and the corresponding coordinate data of the second body surface feature point, can be input into a pre-trained model construction network to improve the accuracy and efficiency of model construction. The feature point is the point with unique local properties. For example, the feature point can be the point where pixel values change drastically, corner point, bifurcation point, etc. In one example, the construction module 10 utilizes feature point detection and matching algorithms to obtain the first body surface feature point, the second body surface feature point, and internal feature point. The feature point detection and matching algorithms may include, for example, Scale-Invariant Feature Transform (SIFT) algorithm, Oriented FAST and Rotated BRIEF (ORB) algorithm, and deep learning-based feature detection and matching algorithms.

After the construction module 10 constructs the first virtual model, deviations in the shape, dimensions, and other aspects of the internal structure between the first virtual model and the corresponding physical anatomical entity may arise. This occurs because the first virtual model is not directly constructed based on real-time CT scanning data or real-time X-ray scanning data. To address this, the calibration module 11 calibrates the first virtual model by using the second virtual model of the living organism to obtain the calibrated first virtual model.

Figure 5:
FIG. 5 shows a schematic diagram of a second virtual model in one embodiment of the present disclosure.

The second virtual model is pre-constructed based on preoperative CT data of the living organism, and the second virtual model includes internal features of the living organism. For example, refer to FIG. 5, which shows a schematic diagram of the second virtual model in one embodiment of the present disclosure. As shown in the figure, the second virtual model of foot includes the internal features of the foot (for example, the shape, size, and pose of each bone). Since the CT data includes multi-layered two-dimensional tomographic scanning data/two-dimensional slice data of the living organism, the second virtual model constructed based on the CT data has high accuracy. In other words, the second virtual model is reliable and matches the real living organism.

Figure 6:
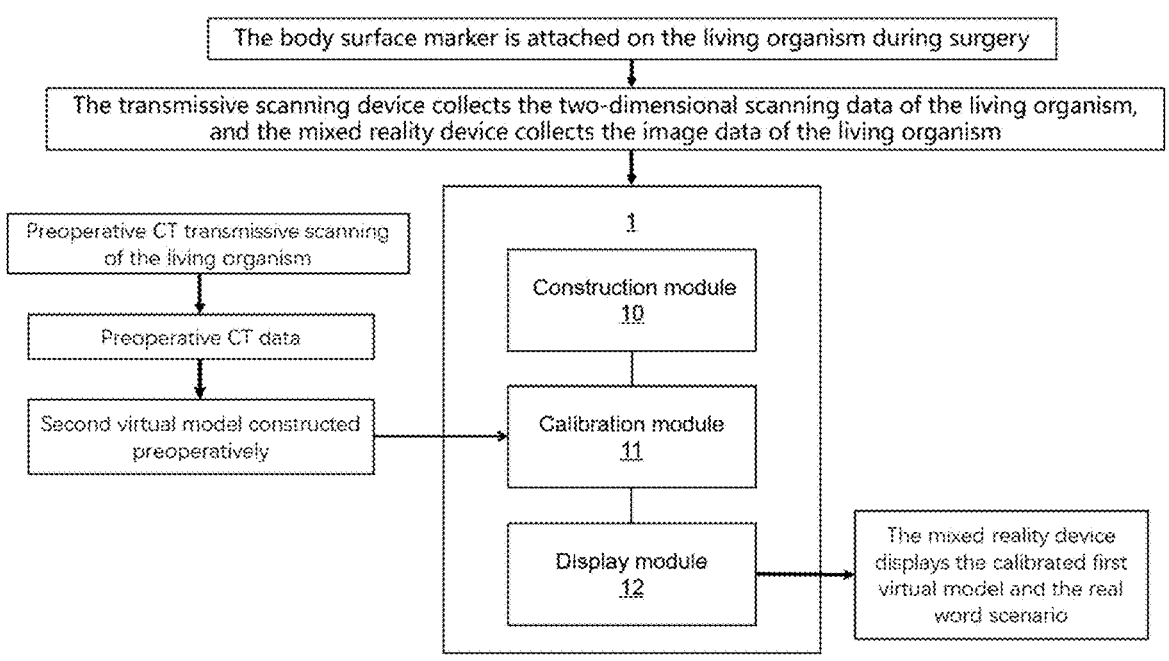
FIG. 6 shows a flowchart of displaying a calibrated first virtual model of the mixed reality device in one embodiment of the present disclosure.

In one embodiment, refer to FIG. 6, which shows a flowchart of displaying the calibrated first virtual model of the mixed reality device in one embodiment of the present disclosure. As shown in the figure, preoperative CT data is acquired by performing transmissive scanning on the living organism using a CT transmissive scanning device. Then, the second virtual model is constructed via three-dimensional reconstruction based on a preset medical three-dimensional reconstruction method and the preoperative CT data, and the second virtual model is transmitted to the calibration module 11. The preset medical three-dimensional reconstruction method includes, for example, surface rendering algorithms (such as the Marching Cubes algorithm) or volume rendering algorithms. The volume rendering algorithms include Ray-Casting Algorithms, Shearing-Warp Algorithms, Frequency-Domain Volume Rendering Algorithms, Splatting Algorithms, etc.

In one embodiment, before the construction of the second virtual model, the preoperative CT data may first undergo denoising and other preprocessing operations. The preprocessed preoperative CT data and three-dimensional model construction methods in the medical field, such as surface rendering algorithms or volume rendering algorithms, are utilized to construct the three-dimensional model. Furthermore, post-processing operations such as defect correction, transparency adjustment, and cross-sectional visualization can also be applied to the constructed second virtual model.

In one embodiment, the second virtual model and the first virtual model are inputs into the pre-trained registration network of the calibration module 11 to obtain the calibrated first virtual model. The exemplary registration network includes the Spatial-Temporal Transformation Network (STN network), Convolutional Neural Network (CNN network), etc. The training method of the registration network will be detailed later.

In another embodiment, the calibration module 11 calibrates the first virtual model based on the coordinate data of the feature points of the internal features in the second virtual model to obtain the calibrated first virtual model. In an embodiment, the coordinate data of multiple feature points (two or more) belonging to the same rigid internal feature is used to calibrate the coordinate data of the corresponding feature points in the first virtual model to obtain the calibrated first virtual model. For example, the coordinate data of multiple feature points (two or more) belonging to the same rigid internal feature is used to determine the dimensions and shape of the rigid internal feature. The determined dimensions and shape are then used to calibrate the coordinate data of the corresponding multiple feature points in the first virtual model, so that the shape and dimensions of the rigid internal feature in the calibrated first virtual model match those of the rigid internal feature in the second virtual model.

Alternatively, the coordinate data of multiple feature points (two or more) belonging to the same rigid internal feature is used to determine the distance between these feature points. The determined distance is then used to calibrate the coordinate data of the corresponding multiple feature points in the first virtual model, ensuring that the distance between the feature points in the calibrated first virtual model matches the distance between the feature points in the second virtual model. The rigid internal features refer to internal features whose shape and dimensions do not change with the movement of the living organism, such as the talus, navicular bone, first phalanx of the great toe, second metatarsal bone of the great toe, and first metatarsal bone in the foot. It should be noted that during calibration, the relative positional relationship between different rigid internal features will not be changed, in order to avoid mismatching the actual pose of the target area during surgery.

Figure 7A:
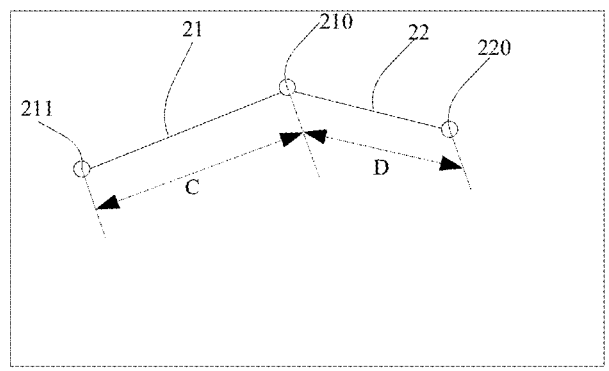
FIG. 7a shows a schematic diagram of a relative pose relationship between feature points on a first metatarsal bone and feature points on a second phalanx of the toe in the first virtual model in one embodiment of the present disclosure.
Figure 7B:
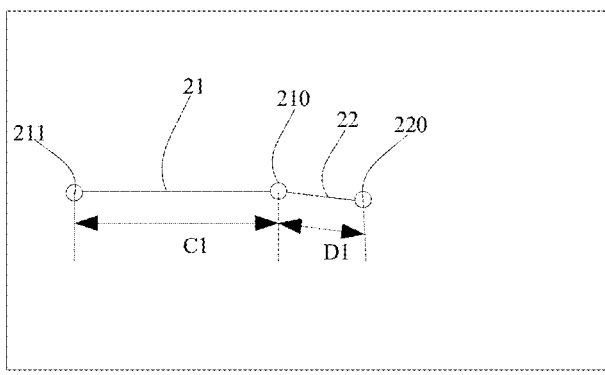
FIG. 7b shows a schematic diagram of a relative pose relationship between feature points on the first metatarsal bone and feature points on the second phalanx of the toe in a second virtual model in one embodiment of the present disclosure.
Figure 7C:
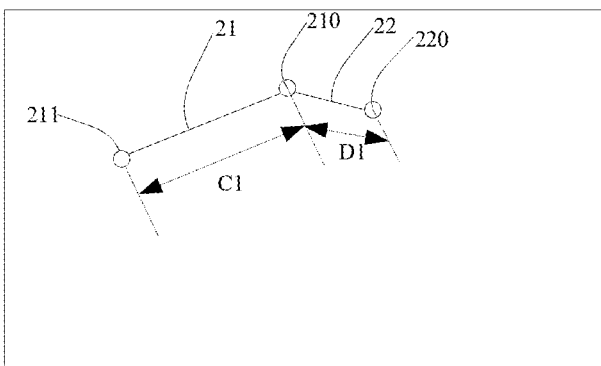
FIG. 7c shows a schematic diagram of a relative pose relationship between feature points on the first metatarsal bone and feature points on the second phalanx of the toe in a calibrated first virtual model in one embodiment of the present disclosure.

In one embodiment, referring to FIGS. 7a to 7c, FIG. 7a shows a schematic diagram of the relative pose relationship between the feature points on the first metatarsal bone and the feature points on the second phalanx of the toe in the first virtual model in one embodiment of the present disclosure. FIG. 7b shows a schematic diagram of the relative pose relationship between the feature points on the first metatarsal bone and the feature points on the second phalanx of the toe in the second virtual model in one embodiment of the present disclosure. FIG. 7c shows a schematic diagram of the relative pose relationship between the feature points on the first metatarsal bone and the feature points on the second phalanx of the toe in the calibrated first virtual model in one embodiment of the present disclosure. As shown in FIG. 7a, based on the coordinate data of two feature points (210, 211) on the first metatarsal bone 21 and the coordinate data of the feature point 220 on the second phalanx of the toe 22, the distance C between the two feature points (210, 211) on the first metatarsal bone 21 and the distance D between the feature point 220 and the feature point 210 on the second phalanx of the toe 22 can be determined. Similarly, as shown in FIG. 7b, based on the corresponding coordinate data in FIG. 7b, the distance between the feature points (210, 211) is C1, and the distance between the feature point 220 and the feature point 210 is D1. The coordinate data of the feature points 211 and 220 shown in FIG. 7a is calibrated based on the distances C1 and D1, so that the coordinate data of the three feature points in the calibrated first virtual model is obtained without changing the relative pose relationship between the first metatarsal bone and the second phalanx of the toe. As shown in FIG. 7c, in the calibrated first virtual model, the distance between the feature point 220 and the feature point 210 is D1, and the distance between the feature points (210, 211) is C1.

After the calibration module 11 obtains the calibrated first virtual model, the display module 12 uses the image data of the body surface marker to determine the pose of the calibrated first virtual model in the real world scenario, so that the calibrated first virtual model and the real world scenario are displayed through the mixed reality device.

In one embodiment, the display module 12 determines the pose of the body surface marker in the real world scenario based on the image data of the body surface marker. And based on the determined pose of the body surface marker in the real world scenario and the pose of the three-dimensional feature of the body surface marker in the calibrated first virtual model, the pose of the calibrated first virtual model in the real world scenario is determined, thereby enabling the calibrated first virtual model and the real world scenario to be displayed through the mixed reality device. It should be noted that, when displayed through the mixed reality device, the real world scenario may be an image of the real world scenario presented by the mixed reality device or the real world scenario observed by the user through the mixed reality device, depending on the configuration of the mixed reality device.

In one embodiment, as shown in FIG. 6, the image data of the living organism is collected using a mixed reality device. Specifically, after the living organism is attached with the body surface marker during surgery, a transmissive scanning device collects the two-dimensional scanning data of the living organism, and the mixed reality device collects the image data of the living organism. The calibration module 11 can determine the pose of the body surface marker in the real world scenario based on the image data of the body surface marker, i.e., the pose of the body surface marker relative to the mixed reality device. Then, based on the pose of the body surface marker in the real world scenario and the pose of the three-dimensional feature of the body surface marker in the calibrated first virtual model, the pose of the calibrated first virtual model in the real world scenario can be determined, i.e., the pose of the calibrated first virtual model relative to the mixed reality device. As a result, the mixed reality device can fuse the calibrated first virtual model with the real world scenario, allowing the user to see both the real world scenario and the calibrated first virtual model in the target area of the living organism through the mixed reality device.

Figure 8:
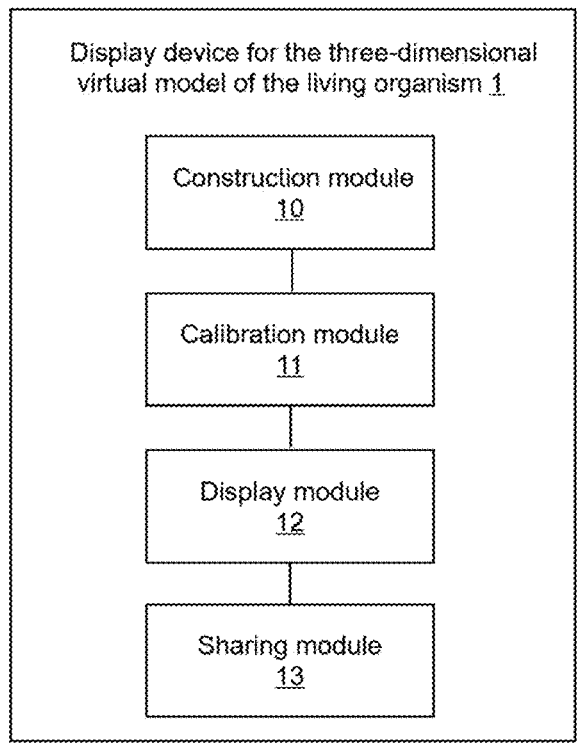
FIG. 8 shows a schematic structural diagram of the display device for the three-dimensional virtual model of the living organism in another embodiment of the present disclosure.

In one embodiment, referring to FIG. 8, which shows a schematic structural diagram of the display device for the three-dimensional virtual model of the living organism in another embodiment of the present disclosure. As shown in the figure, the display device for the three-dimensional virtual model of the living organism 1 further includes a sharing module 13. The sharing module 13 is configured to transmit the display data of the mixed reality device to the sharing device connected with the mixed reality device for display. In this way, a user can also observe the display content seen by the user wearing the mixed reality device (e.g., the lead surgeon) through the sharing device. The sharing device may include, for example, a computer device or another mixed reality device.

Additionally, the sharing module is further configured to display the calibrated first virtual model, which is sent from the sharing device belonging to the whitelist and configured with annotation information, on both the mixed reality device and all the sharing devices. In this way, in the case of remote surgery, the remote doctor can interact with the displayed calibrated first virtual model by wearing the sharing device of a mixed reality device. For example, when annotation information about the displayed calibrated first virtual model is provided, the doctor in the operating room can observe these annotation information marked by the remote doctor in real time. The annotation information may include, for example, surgical paths, puncture points, etc.

Figure 9:
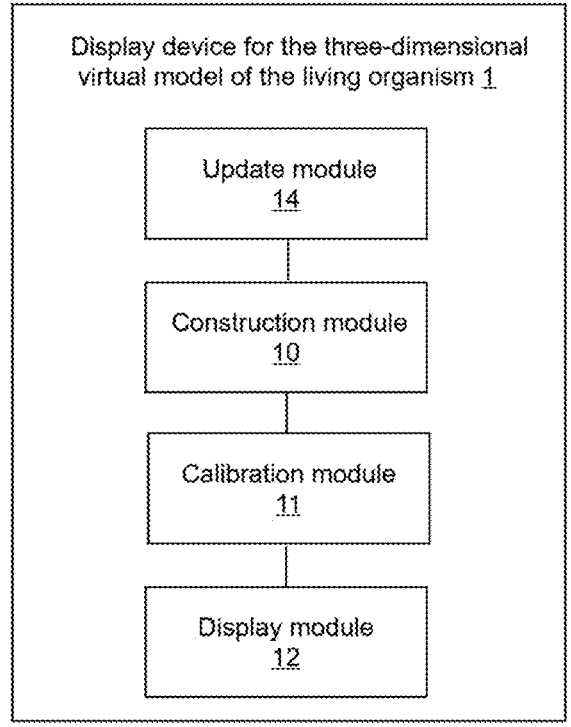
FIG. 9 shows a schematic structural diagram of the display device for the three-dimensional virtual model of the living organism in another embodiment of the present disclosure.

In one embodiment, referring to FIG. 9, which shows a schematic structural diagram of the display device for the three-dimensional virtual model of the living organism in another embodiment. As shown in the figure, the display device for the three-dimensional virtual model 1 further includes an update module 14. The update module 14 is configured to update the image data of the living organism, so that the construction module 10 can update the first virtual model, the calibration module 11 can calibrate the updated first virtual model, and the display module 12 can display the calibrated updated first virtual model and the real world scenario through the mixed reality device. This ensures that when the pose of the target area of the living organism changes, the calibrated updated first virtual model displayed through the mixed reality device matches the current pose of the target area, achieving precise alignment between the three-dimensional virtual model and corresponding physical anatomical entity of the living organism and widening application in actual clinical surgeries. The pose of the target area refers to the shape or state presented by the target area. For example, if the target area is the foot, the pose of the foot includes, but is not limited to, toes together, toes spread apart, dorsum of the foot in a neutral position, dorsum of the foot flexed, toes flexed, and toes extended.

In a specific embodiment, the mixed reality device acquires the image data of the living organism in real time. When the update module 14 detects a change in the image data of the living organism, it updates the image data accordingly. The construction module 10 then updates the first virtual model based on the updated image data of the living organism. The calibration module 11 calibrates the updated first virtual model based on the second virtual model to obtain the calibrated updated first virtual model. The display module 12 determines the pose of the calibrated updated first virtual model in the real world scenario based on the updated image data of the body surface marker, and then displays the calibrated updated first virtual model and the real world scenario through the mixed reality device. In one embodiment, the update module 14 determines whether the image data of the living organism has changed, based on the real-time acquired image data and a preset rule. When a change in the position, pose, and/or posture of the target area of the living organism changes, the preset rule determines the image data of the living organism has changed. For example, when the foot changes from a dorsum extended position to a dorsum flexed position, it can be determined that the posture of the target area has changed. Similarly, if the foot moves from the left side of the operating table to the right side, it can be determined that the position of the target area has changed. Furthermore, if the foot changes from being parallel to the operating table to forming an angle with it, it can be determined that the posture of the target area has changed.

In one embodiment, based on the updated image data of the living organism, the construction module 10 also determines whether any changes have occurred in the target surgical area and its surrounding preset area. If no changes are detected, the construction module does not update the first virtual model. Otherwise, the construction module updates the first virtual model based on the updated image data of the living organism. In this way, it allows for real-time visualization of the actual state of the surgical area through the virtual model while avoiding the additional computational load caused by frequently updating the first virtual model.

To obtain the pre-trained model construction network mentioned above, in one embodiment, the display device for the three-dimensional virtual model further includes a first training module (not shown in the figures). The first training module is configured to train the network parameters of a model construction network by using the first sample data until the loss function of the model construction network converges to a preset threshold to obtain the pre-trained model construction network. For the sake of distinction, in the following embodiments, the preset threshold used in training the model construction network will be referred to as the first preset threshold, and the preset threshold used in training the registration network will be referred to as the second preset threshold.

In one embodiment, the first sample data includes a third virtual model (real sample) that is pre-constructed by using the CT data of the body surface and interior of the living organism, as well as the two-dimensional scanning data and the image data of the corresponding living organism. In other words, the first sample data includes multiple sets of the two-dimensional scanning data, the image data, and the pre-constructed third virtual model belonging to the same living organism. Furthermore, the first sample data also includes pre-determined first body surface feature point, second body surface feature point, and internal feature point in the two-dimensional scanning data, in order to improve the training speed. In the following embodiments, the first sample data including multiple sets of the two-dimensional scanning data, the image data, and the pre-constructed third virtual model belonging to the same living organism is taken as an example for illustration.

In one embodiment, both the two-dimensional scanning data and the image data are respectively pre-provided with a first preset label which contains label information used to represent a pairwise relationship. In other words, the first preset label includes label information used to indicate whether the two-dimensional scanning data and the image data belong to the same living organism.

In one embodiment, the model construction network is a Generative Adversarial Network (GAN) and consists of a generator and a discriminator. During the training process, the first training module inputs the two-dimensional scanning data and image data of multiple living organisms from the first sample data as well as random noise into the generator, enabling the generator to generate multiple first virtual models. The first training module inputs the corresponding third virtual models (real sample) of multiple living organisms and the first virtual models generated by the generator into the discriminator, allowing the discriminator to output a discrimination result. The discrimination result includes whether the input model is a real sample or a generated sample, and the probability value corresponding to the real sample or generated sample. Subsequently, the first training module calculates the loss function of the Generative Adversarial Network based on the discrimination result, the generated first virtual model, and the third virtual model. The model parameters of the Generative Adversarial Network are then adjusted until the loss function of the Generative Adversarial Network reaches the first preset threshold. In one embodiment, the value of the first preset threshold ranges from 0.45 to 0.55. For example, the value of the first preset threshold may be 0.45, 0.46, 0.47, 0.48, 0.49, 0.50, 0.51, 0.52, 0.53, 0.54, or 0.55.

The loss function L1 of the Generative Adversarial Network is $L_{gen}+L_{ce}$, wherein $L_{gen}$ is the generation loss of the generator, and Lee is the classification loss of the discriminator. In one embodiment, the classification loss Lee is a cross-entropy loss, and the generation loss $L_{gen}$ is a three-dimensional reconstruction loss. For example, the three-dimensional reconstruction loss may be represented as: $\alpha y_g$ log $(y_e)-(1-\alpha)(1-y_g)$ log $(1-y_e)$; wherein a is a preset constant, $y_g$ is a three-dimensional voxel of the third virtual model, and $y_e$ is a three-dimensional voxel of the generated first virtual model.

It should be noted that the model construction network, which is a Generative Adversarial Network (GAN), can improve the construction accuracy of the first virtual model. However, in other embodiments, the model construction network may also be any one of the networks described above.

To obtain the aforementioned pre-trained registration network, in one embodiment, the display device further includes a second training module (not shown in the figures). The second training module is configured to train the network parameters of a registration network by using the second sample data until a loss function of the registration network converges to a second preset threshold to obtain the pre-trained registration network. The second sample data includes the second virtual model of the living organism and the corresponding first virtual model. Furthermore, both the second virtual model and the first virtual model are respectively pre-provided with a second preset label, which contains label information used to indicate whether the second virtual model and the first virtual model belong to the same living organism.

In one embodiment, the second training module inputs multiple second virtual models and corresponding first virtual models into the registration network and outputs the calibrated first virtual models. The second training module calculates the loss function of the registration network based on the internal features of the calibrated first virtual model and the corresponding second virtual model, and adjusts the model parameters of the registration network until the loss function of the registration network converges to a second preset threshold. The loss function of the registration network is, for example, a shape matching loss function or a geometric loss function. The shape matching loss function is, for example, the Intersection over Union (IoU) loss function. The value of the second preset threshold ranges from 0 to 0.05. For example, the value of the second preset threshold may be 0, 0.01, 0.02, 0.03, 0.04, or 0.05.

In summary, the display device for the three-dimensional virtual model of the living organism provided in the present disclosure constructs the first virtual model by using the two-dimensional scanning data and the image data of the living organism collected during surgery. This ensures that the body surface features and internal features of the first virtual model match the actual state/pose of the target area of the living organism during surgery, facilitating precise alignment between the three-dimensional virtual model and the corresponding physical anatomical entity. Moreover, after calibrating the first virtual model using the second virtual model constructed preoperatively, the dimensions of the internal features in the calibrated first virtual model match the actual dimensions of the internal features of the living organism, further ensuring the precise alignment between the three-dimensional virtual model and the corresponding physical anatomical entity. Additionally, by using body surface marker attached on the body surface, the calibrated first virtual model can be fused with the real world scenario for display without the need of invasive procedures for exposing internal structures, ultimately achieving precise alignment between the three-dimensional virtual model and the corresponding physical anatomical entity.

Furthermore, the display device for the three-dimensional virtual model of the living organism provided in this disclosure can reduce the surgical cost compared to employing positioning targets and facilitate clinical surgical applications. Additionally, during surgery, the mixed reality device detects the image data of the living organism in real time and tracks the target area of the living organism and displays the calibrated first virtual model in real time. This eliminates the need of an optical tracking system that occupies a large space. As a result, the solution provided in the present disclosure avoids issues such as the inability to acquire the image data beyond 2 meters or the loss of the image (the loss of virtual model), as well as signal delays and image jitter caused by the signal transmission between multiple devices, and is low cost due to without the use of an optical tracking system. Specifically, by using the update module to update the image data of the living organism in real time and display the calibrated updated first virtual model, the present disclosure ensures that the displayed three-dimensional virtual model remains alignment with the actual target area of the living organism, even if the target area changes during surgery. This contributes to the smooth progress of the surgery.

Although in the prior art, a one-time intraoperative scanning data of the body surface contour can be used before carrying out a surgery to construct a body surface contour model with markers, and the structural model preoperatively constructed, which includes both the body surface features and internal features, can be fused with the body surface contour model to obtain a surgical guidance model that includes the internal features and the body surface contour, allowing the doctor to determine the surgical path based on the surgical guidance model and markers on the corresponding physical anatomical entity. However, since the above-mentioned solution assumes that the target area of the human body does not change during surgery and that the internal features is pre-marked with surgical path information, the surgical guidance model generated based on the preoperative internal features may be inconsistent with the pose of the target area during surgery due to changes in the pose of the body posture.

In contrast to the aforementioned prior art, the present disclosure ensures that the displayed virtual model matches the actual state/pose of the target area. In the aforementioned prior art, the body surface contour data is obtained through a one-time scanning, meaning that the prior art cannot update the surgical guidance model based on the real-time state of the human body. The present disclosure can display the updated three-dimensional virtual model in real time based on the updated image data, ensuring that the state of the three-dimensional virtual model consistently matches the state of the target area at every moment. Additionally, in the aforementioned prior art, the surgical guidance model is not displayed through the mixed reality device, causing doctors' focus to constantly switch between the computer screen and the human body and making low efficiency for guiding the surgery. Furthermore, the present disclosure can display the calibrated first virtual model through the mixed reality device, eliminating the need for switching of perspectives and thus improving the efficiency of the surgery.

The present disclosure also discloses a display system for a three-dimensional virtual model of a living organism, wherein the display system includes the display device for the three-dimensional virtual model of the living organism as described above. For example, the modules of the display device for the three-dimensional virtual model of the living organism are included in the computer device and mixed reality device in the display system, enabling the display system to perform the functions of each module.

Figure 10:
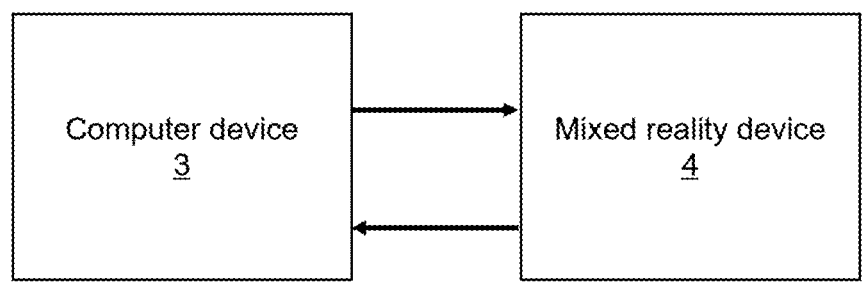
FIG. 10 shows a schematic structural diagram of a display system for a three-dimensional virtual model of the living organism in one embodiment of the present disclosure.

Please refer to FIG. 10, which shows a schematic structural diagram of the display system for the three-dimensional virtual model of the living organism in an embodiment of the present disclosure. As shown in the figure, the display system includes a computer device 3 and a mixed reality device 4. The computer device 3 and the mixed reality device 4 are communicatively connected to allow data transmission between the two. Specifically, the computer device 3 is configured to construct a first virtual model comprising the body surface features and internal features of the living organism based on the two-dimensional scanning data and image data of the living organism collected during surgery; and to calibrate the first virtual model by using the second virtual model of the living organism to obtain a calibrated first virtual model. The mixed reality device 4, connected to the computer device 3, is configured to determine the pose of the calibrated first virtual model in the real world scenario based on the image data of the surface marker, so as to display the calibrated first virtual model and the real world scenario.

Figure 11:
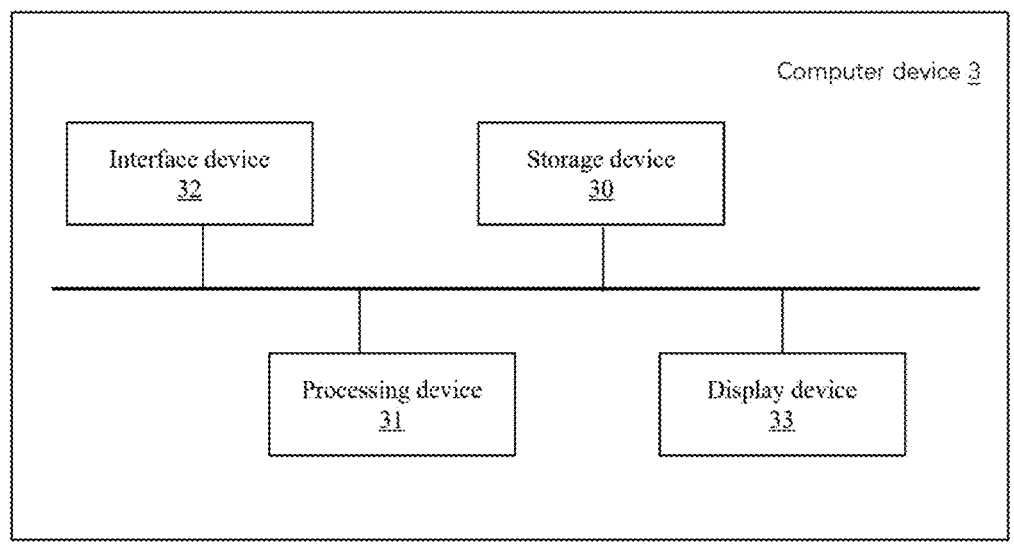
FIG. 11 shows a schematic structural diagram of a computer device in one embodiment of the present disclosure.

In one embodiment, please refer to FIG. 11, which shows a schematic structural diagram of the computer device in one embodiment of the present disclosure. As shown in the figure, the computer device 3 includes a storage device 30, a processing device 31 connected to the storage device 30, and an interface device 32.

In some embodiments, the storage device 30 is configured to store at least one program, and the storage device 30 includes, but is not limited to: read-only memory, random access memory, and non-volatile memory. For example, the storage device 30 includes a flash memory device or other non-volatile solid-state storage devices. In certain embodiments, the storage device 30 may also include a memory located remotely away from one or more processing devices 31, such as a network-attached memory that is accessed via RF circuits, external ports, or communication network. The communication network may include the Internet, one or more intranets, local area networks, wide area networks, storage area networks, or any appropriate combination thereof. The memory controller may control access to the memory by other components of the device, such as the CPU and peripheral interfaces.

In one embodiment, the storage device 30 is also configured to store the second virtual model or the collected two-dimensional scanning data of the living organism, etc., to allow the computer device 3 to construct and calibrate the first virtual model.

In some embodiments, the interface device 32 is configured to communicatively connect to the mixed reality device 4 to receive the image data of the living organism obtained by the mixed reality device 4. The interface device 32 includes at least one interface unit, and these interface units are configured to output a visualization interface and receive human-computer interaction events generated according to the user's actions, and so on. For example, the interface device 32 includes, but is not limited to: serial interfaces such as HDMI or USB interfaces, or parallel interfaces, etc. In one embodiment, the interface device 32 further includes a network communication unit, which is configured to transmit data via wired or wireless networks. Examples of the network communication unit include, but are not limited to: integrated circuits with network cards, local area network modules such as WiFi modules or Bluetooth modules, and wide area network modules such as mobile network modules.

In some embodiments, the interface device 32 is also configured to receive the display data which is synchronously transmitted from the mixed reality device 4. The display data includes the real world scenario and virtual objects that the user sees through the mixed reality device 4.

In some embodiments, the interface device 32 is also configured to send the calibrated first virtual model to the mixed reality device 4.

In some embodiments, the processing device 31, connected to the storage device 30, is configured to invoke and execute at least one program from the storage device 30, to construct the first virtual model comprising the body surface features and internal features based on the two-dimensional scanning data and the image data of the living organism collected during surgery; and to calibrate the first virtual model by using a second virtual model of the living organism to obtain a calibrated first virtual model. The method for constructing and calibrating the first virtual model is the same as or similar to the method described above and will not be repeated here.

In some embodiments, the processing device 31 includes one or more processors. The processing device 31 is operatively connected to the storage device 30 to perform data read/write operations. The processing device 31 includes one or more general-purpose microprocessors, application-specific integrated circuits (ASICs), digital signal processors, and field-programmable gate arrays (FPGAs). In one embodiment, the application-specific integrated circuit includes a graphics processor.

In one embodiment, as shown in FIG. 11, the computer device 3 further includes a display device 33. The display device 33 may be, for example, the monitor or touchscreen of the computer device 3.

In an embodiment, when the computer device 3 includes the display device 33, the processing device 31 is further configured to display the display data, which is received from the interface device 32 and synchronously transmitted from the mixed reality device 4, on the display device 33. In this way, users not wearing the mixed reality device can also see the calibrated first virtual model and the real world scenario through the computer device 3 during surgery.

In one embodiment, the mixed reality device 4 can fuse virtual objects (such as the calibrated first virtual model or the calibrated updated first virtual model) with the real world scenario for display; additionally, users can interact with the virtual objects. The mixed reality device 4 may be, for example, a head-mounted mixed reality device (e.g., mixed reality glasses). In one embodiment, the mixed reality device 4 can include one or more sensors (such as depth sensors, cameras, etc.) for scanning or collecting information from the real world scenario (e.g., operating room, etc.), as well as a circuit system for transmitting the collected information to another device (such as a server, workstation, desktop computer, laptop, tablet, smartphone, etc.). Furthermore, the mixed reality device 4 can include a wireless interface for connecting to the Internet, the local wireless network, or another computer device.

In one embodiment, the mixed reality device 4 can also be configured to receive audio/gesture input from the user. The gesture or audio inputs can be voice commands or recognized user gestures, which, when detected by the mixed reality device 4, enable the mixed reality device to execute the corresponding commands. The gestures can be the recognizable gesture described in subsequent embodiments. In one embodiment, the mixed reality device 4 is preferably lightweight and no use of heavy components that could make the mixed reality device 4 uncomfortable to wear. For example, the mixed reality device 4 could be in the form of mixed reality glasses, which are lightweight to ensure minimal load for the head of users during surgery.

The mixed reality device 4 may be configured to determine a display area in the real world scenario to display the virtual object within the display area, thereby enabling the user to see the virtual object within the display area. Furthermore, the mixed reality device 4 may also provide the image data and the depth data to a mobile processor and receive display information from the mobile processor. The mobile processor and the mixed reality device 4 are individual components, which is shown in detail as FIG. 10.

In the present disclosure, the mixed reality device 4 can render virtual objects displayed within the display area to provide a mixed reality experience, which facilitates interaction with the computer device and collaboration with other users.

Figure 12:
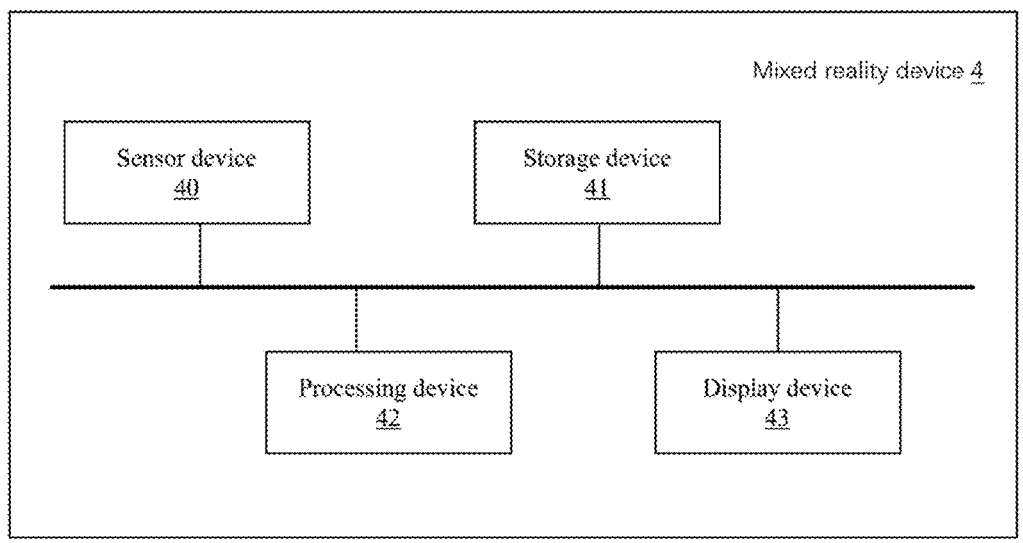
FIG. 12 shows a schematic structural diagram of a mixed reality device in one embodiment of the present disclosure.

Please refer to FIG. 12, which shows the schematic structural diagram of the mixed reality device in one embodiment of the present disclosure. As shown in the figure, the mixed reality device 4 includes a sensor device 40, a storage device 41, a processing device 42, and a display device 43.

The sensor device 40 is used to collect the image data of the living organism. In some embodiments, the sensor device 40 includes at least one sensor. In embodiments where the sensor device 40 includes multiple sensors, the multiple sensors may either be the same type or different types.

In one embodiment, the sensor device 40 includes a camera, which is configured to provide the image data of the living organism to the processing device 42. Furthermore, the sensor device 40 may also include a depth sensor, which is configured to provide the depth data to the processing device 42. Based on the depth data, the processing device 42 can determine the distance of an object relative to the mixed reality device 4.

In some embodiments, the storage device 41 is configured to store at least one program. The at least one program is available for execution by the processing device 42. The storage device 41 includes, but is not limited to: read-only memory, random access memory, non-volatile memory. For example, the storage device 41 includes a flash memory device or other non-volatile solid-state storage devices. In certain embodiments, the storage device 41 may also include a memory located remotely away from one or more processing devices 42, such as a network-attached memory that is accessed via RF circuits, external ports, or communication network. The communication network may include the Internet, one or more intranets, local area networks, wide area networks, storage area networks, or any appropriate combination thereof. The memory controller may control access to the memory by other components of the device, such as the CPU and peripheral interfaces.

The display device 43 is configured to fuse the virtual model with the real world scenario, allowing the user to see both the virtual object and the real world scenario through the display device 43. For example, the display device 43 determines the display area of the calibrated first virtual model based on the determined pose of the calibrated first virtual model in the real world scenario, and then fuses the calibrated first virtual model with the real world scenario for display.

In one embodiment, the display device 43 is a semi-transparent display device, allowing the user to see the real world scenario through the display device 43, while the display device 43 can also display the virtual model (e.g., the calibrated first virtual model) such that the virtual model can be anchored to the display area seen by the user through the display device 43. In this way, the user can watch the real world scenario through a semi-transparent head-mounted display device, wherein objects in the real world scenario (such as a bed or a living organism) are visible through the head-mounted display device, while the virtual model is shown within this visible scene. The virtual model can be anchored to or linked with the real world objects. This embodiment provides a mixed reality experience.

In one embodiment, the display device 43 is a display device based on video compositing technology. Specifically, the processing device 42 (such as a graphics processor) receives the image information from the real world scenario acquired by the sensor device 40. After processing the information, it fuses the virtual model into the real world scenario. Finally, the processing device 42 controls the display device 43 to show the synthesized image to the user. In one example, the display device based on video compositing technology includes a monitor.

In one embodiment, the display device 43 is an optical-based display device, for example, a holographic display device. The processing device 43 controls the optical-element-based display device to first project the virtual model directly onto an optical element unit, and then the virtual object will be delivered into the human eyes through the reflection of the optical element unit. Meanwhile, the real world scenario image will directly be transmitted to the human eyes through the optical element unit. As a result, the user can see both the real world scenario and the virtual object simultaneously.

In one embodiment, the optical-based display device includes a monitor and an optical element unit. The optical element unit includes a semi-transparent and semi-reflective mirror, a holographic diffraction waveguide grating, or other suitable optical elements. In this embodiment, the processing device controls the monitor to show the virtual model at a preset position and preset pose. The optical element unit is configured to reflect the virtual model displayed on the monitor into the human field of vision and to transmit light from the real world scenario.

It should be noted that the description of the display device in the present disclosure is merely an example. In other embodiments, the display device could also include elements such as optical waveguides.

In some embodiments, the processing device 42, connected to the storage device 41, display device 43, and sensor device 40, is configured to invoke and execute the at least one program from the storage device 41, so as to determine the pose of the calibrated first virtual model in the real world scenario based on the image data of the body surface marker and display the calibrated first virtual model and the real world scenario through the mixed reality device 4.

In some embodiments, the processing device 42 includes one or more processors. The processing device 42 is operatively connected to the storage device 41 to perform data read/write operations. The processing device 42 includes one or more general-purpose microprocessors, application-specific integrated circuits (ASICs), digital signal processors, field-programmable gate arrays (FPGAs). In one embodiment, the application-specific integrated circuit includes a graphics processor.

In one embodiment, the mixed reality device 4 also includes an interface device (not shown in the figures), which is configured to communicate with the computer device 3. Furthermore, the interface device is also configured to communicate with the sharing device. The interface device includes, but is not limited to, serial interfaces such as HDMI or USB interfaces, or parallel interfaces. In one embodiment, the interface device further includes a network communication unit, which is configured to transmit data via wired or wireless networks. Examples of the network communication unit include, but are not limited to: integrated circuits with network cards, local area network modules such as WiFi modules or Bluetooth modules, and wide area network modules such as mobile network modules.

In one embodiment, the display system also includes a sharing device (not shown in the figures) communicatively connected to the mixed reality device 4. The sharing device is configured to synchronously display the display data from the mixed reality device 4. In this way, users (either users in the operating room or remote users wearing the sharing device) can observe the display content seen by the user wearing the mixed reality device 4 (e.g., lead surgeon) through the sharing device, which facilitates surgical cooperation, surgical teaching, and remote surgeries.

In one embodiment, the display system (e.g., computer device 3) can also receive the calibrated first virtual model, which is sent from the sharing device belonging to the whitelist and provided with annotation information, in order to display the calibrated first virtual model on the mixed reality device 4 and all sharing devices.

The present disclosure also provides a mixed reality device. Please refer to FIG. 12. The mixed reality device includes a sensor device 40, storage device 41, processing device 42, and display device 43. The structure and functions of the sensor device 40, storage device 41, and display device 43, as well as the structure of the processing device 42, are the same as or similar to those described above, and will not be repeated here.

In one embodiment, the mixed reality device is combined with a surgical navigation system to assist doctors in performing surgical operations. In this embodiment, the surgical navigation system is an electronic system that provides guidance information to assist the user in performing surgical operations. The guidance information includes: graphics or data representing the relative positional relationship between the surgical instruments and the surgical site, and/or the surgical path, to provide the user with real-time guidance information.

In one embodiment, the mixed reality device 4 can fuse virtual objects (e.g., the calibrated first virtual model or the calibrated updated first virtual model) with the real world scenario for display; additionally, users can interact with the virtual objects. The mixed reality device 4 may be, for example, a head-mounted mixed reality device (e.g., mixed reality glasses). In one embodiment, the mixed reality device 4 can include one or more sensors (e.g., depth sensors, cameras, etc.) for scanning or collecting information from the real world scenario (e.g., operating room, etc.), as well as a circuit system for transmitting the collected information to another device (e.g., a server, workstation, desktop computer, laptop, tablet, smartphone, etc.). Furthermore, the mixed reality device 4 can include a wireless interface for connecting to the Internet, the local wireless network, or another computer device.

In one embodiment, the mixed reality device 4 can also be configured to receive audio/gesture inputs from the user. The audio/gesture inputs can be voice commands or recognized user gestures, which, when detected by the mixed reality device 4, enable the mixed reality device to execute the corresponding commands. The gesture can be the recognizable gesture described in subsequent embodiments. In one embodiment, the mixed reality device 4 is preferably lightweight and no use of heavy components that could make the mixed reality device 4 uncomfortable to wear. For example, the mixed reality device 4 could be in the form of mixed reality glasses, which are lightweight to ensure minimal load for the head of users during surgery.

The mixed reality device 4 may be configured to determine a display area in the real world scenario to display the virtual object within the display area, thereby enabling the user to see the virtual object within the display area. Furthermore, the mixed reality device 4 may also provide the image data and the depth data to a mobile processor and receive display information from the mobile processor. The mobile processor and the mixed reality device 4 are individual components, which is shown in detail as FIG. 10.

In the present disclosure, the mixed reality device 4 can render virtual objects displayed within the display area to provide a mixed reality experience, which facilitates interaction with the computer device and collaboration with other users. The processing device 42, connected to the sensor device 40, the storage device 41, and the display device 43, is configured to invoke and execute at least one program from the storage device to achieve the following: constructing a first virtual model comprising body surface features and internal features of the living organism based on the two-dimensional scanning data and the image data of the living organism collected during surgery; calibrating the first virtual model by using a second virtual model of the living organism to obtain a calibrated first virtual model; and determining the pose of the calibrated first virtual model in a real world scenario based on the image data of the body surface marker to display the calibrated first virtual model and the real world scenario through the mixed reality device. The method of constructing and calibrating the first virtual model, as well as displaying the calibrated first virtual model and the real world scenario through the mixed reality device, is the same as or similar to the method described above, and will not be repeated here.

Those skilled in the art will recognize that the various units and algorithmic steps described in the exemplary embodiments disclosed herein can be implemented using electronic hardware, or a combination of computer software and electronic hardware. Whether these functions are implemented by hardware or software depends on the specific application and design constraints of the technical solution. Those skilled in the art may adopt different methods to implement the described functions for each specific application, but such implementations should not be considered beyond the scope of the present disclosure.

In summary, the present disclosure provides a display device and system for a three-dimensional virtual model of a living organism, as well as a mixed reality device. By constructing a first virtual model based on the two-dimensional scanning data and the image data of the living organism collected during surgery, the display device and system ensure that the body surface features and internal features of the first virtual model correspond to the actual pose of the target area of the living organism during surgery. Furthermore, by calibrating the first virtual model with the second virtual model constructed preoperatively, the dimensions of the internal features in the calibrated first virtual model match the actual dimensions of the internal features of the living organism. Through the body surface marker attached on the body surface, the calibrated first virtual model can be fused with the real world scenario for display without the need for invasive procedures, achieving precise alignment between the three-dimensional virtual model and the corresponding physical anatomical entity, thereby facilitating clinical surgical applications. Furthermore, the two-dimensional scanning data of the living organism includes anteroposterior and lateral X-ray data and the first virtual model is calibrated through the second virtual model, which not only reduces the radiation exposure of the living organism but also ensures the accuracy of the display of virtual model.

The above-mentioned embodiments are merely illustrative of the principle and effects of the present disclosure instead of limiting the present disclosure. Modifications or variations of the above-described embodiments may be made by those skilled in the art without departing from the principle and scope of the present disclosure. Therefore, all equivalent modifications or changes made by those who have common knowledge in the art without departing from the spirit and technical concept disclosed by the present disclosure shall be still covered by the claims of the present disclosure.

What is claimed is:

1. A display device for a three-dimensional virtual model of a living organism, comprising:
    a construction module, configured to construct a first virtual model comprising body surface features and internal features of a living organism based on two-dimensional scanning data and image data of the living organism collected during surgery; wherein the two-dimensional scanning data of the living organism includes scanning data of a body surface marker and internal tissue of a target area of the living organism, and the image data of the living organism includes image data of a body surface marker and body surface of the target area of the living organism; wherein constructing the first virtual model comprising the body surface features and internal features of the living organism based on the two-dimensional scanning data and the image data of the living organism collected during surgery comprises: inputting the two-dimensional scanning data and the image data of the living organism into a pre-trained model construction network to obtain the first virtual model;
    a calibration module, configured to calibrate the first virtual model by using a second virtual model of the living organism to obtain a calibrated first virtual model; wherein the second virtual model is pre-constructed based on preoperative CT data of the living organism, and the second virtual model includes the internal features of the living organism; wherein calibrating the first virtual model by using the second virtual model of the living organism to obtain the calibrated first virtual model comprises:
        calibrating coordinate data of multiple feature points in the first virtual model based on coordinate data of multiple feature points of rigid internal features in the second virtual model that correspond to the rigid internal features in the first virtual model, so as to ensure that the shape and dimensions of the rigid internal features in the calibrated first virtual model match those of the rigid internal features in the second virtual model; or
        inputting the first virtual model and the second virtual model of the living organism into a pre-trained registration network to obtain the calibrated first virtual model;
    a display module, configured to determine a pose of the calibrated first virtual model in a real world scenario based on the image data of the body surface marker to display the calibrated first virtual model and the real world scenario through a mixed reality device.

2. The display device for the three-dimensional virtual model of the living organism of claim 1, wherein the two-dimensional scanning data of the living organism is collected during surgery by using a transmissive scanning device to visualize the target area of the living organism, wherein the body surface marker is attached on the body surface of the target area.

3. The display device for the three-dimensional virtual model of the living organism of claim 2, wherein the two-dimensional scanning data of the living organism comprises anteroposterior X-ray data and lateral X-ray data of the target area of the living organism.

4. The display device for the three-dimensional virtual model of the living organism of claim 1, wherein the body surface marker comprises a physical object or pattern marker that is detected by a transmissive scanning device.

5. The display device for the three-dimensional virtual model of the living organism of claim 1, wherein the image data of the living organism is collected in real time during surgery by the mixed reality device.

6. The display device for the three-dimensional virtual model of the living organism of claim 1, wherein calibrating the first virtual model by using the second virtual model of the living organism to obtain the calibrated first virtual model comprises: calibrating the first virtual model based on coordinate data of feature points of the internal features in the second virtual model to obtain the calibrated first virtual model.

7. The display device for the three-dimensional virtual model of the living organism of claim 1, wherein determining the pose of the calibrated first virtual model in the real world scenario based on the image data of the body surface marker to display the calibrated first virtual model and the real world scenario through the mixed reality device comprises:
    determining a pose of the body surface marker in the real world scenario based on the image data of the body surface marker;
    based on the pose of the body surface marker in the real world scenario and features of the body surface marker in the calibrated first virtual model, determining the pose of the calibrated first virtual model in the real world scenario to display the calibrated first virtual model and the real world scenario through the mixed reality device.

8. The display device for the three-dimensional virtual model of the living organism of claim 1, wherein the display device further comprises a sharing module, configured to transmit display data of the mixed reality device to a sharing device connected with the mixed reality device for display on the sharing device.

9. The display device for the three-dimensional virtual model of the living organism of claim 1, wherein the display device further comprises an update module, configured to update the image data of the living organism, which allows the construction module to update the first virtual model.

10. The display device for the three-dimensional virtual model of the living organism of claim 9, wherein the update module updates the image data of the living organism when the update module determines that the image data of the living organism has changed.

11. The display device for the three-dimensional virtual model of the living organism of claim 1, wherein the display device further comprises a first training module, configured to train network parameters of a model construction network by using first sample data until a loss function of the model construction network converges to a preset threshold to obtain the pre-trained model construction network; wherein the first sample data comprises a third virtual model pre-constructed by using CT data of body surface and interior of the living organism, as well as the two-dimensional scanning data and the image data of the living organism.

12. The display device for the three-dimensional virtual model of the living organism of claim 1, wherein the display device further comprises a second training module, configured to train network parameters of a registration network by using second sample data until a loss function of the registration network converges to a preset threshold to obtain the pre-trained registration network; wherein the second sample data comprises the second virtual model and the corresponding first virtual model.

13. A display system of a three-dimensional virtual model of a living organism, comprising:
   a computer device, configured to construct a first virtual model comprising body surface features and internal features of the living organism based on two-dimensional scanning data and image data of the living organism collected during surgery; and to calibrate the first virtual model by using a second virtual model of the living organism to obtain a calibrated first virtual model; wherein the two-dimensional scanning data comprises scanning data of a body surface marker and internal tissue of a target area of the living organism, and the image data of the living organism comprises image data of a body surface marker and body surface of the target area of the living organism; wherein the second virtual model is pre-constructed based on pre-operative CT data of the living organism, and the second virtual model comprises internal features of the living organism;
      wherein constructing the first virtual model comprising the body surface features and internal features of the living organism based on the two-dimensional scanning data and the image data of the living organism collected during surgery comprises: inputting the two-dimensional scanning data and the image data of the living organism into a pre-trained model construction network to obtain the first virtual model;
      wherein calibrating the first virtual model by using the second virtual model of the living organism to obtain the calibrated first virtual model comprises:
         calibrating coordinate data of multiple feature points in the first virtual model based on coordinate data of multiple feature points of rigid internal features in the second virtual model that correspond to the rigid internal features in the first virtual model, so as to ensure that the shape and dimensions of the rigid internal features in the calibrated first virtual model match those of the rigid internal features in the second virtual model; or
         inputting the second virtual model and the first virtual model of the living organism into a pre-trained registration network to obtain the calibrated first virtual model;
   a mixed reality device, connected to the computer device, configured to determine a pose of the calibrated first virtual model in a real world scenario based on the image data of the body surface marker to display the calibrated first virtual model and the real world scenario.

14. A mixed reality device, comprising:
   a sensor device, configured to collect image data of a living organism;
   a storage device, configured to store at least one program;
   a display device, configured to fuse a virtual model with a real world scenario for display;
   a processing device, connected to the sensor device, storage device, and display device, configured to invoke and execute the at least one program from the storage device to achieve the following:
   constructing a first virtual model comprising body surface features and internal features of the living organism based on two-dimensional scanning data and image data of the living organism collected during surgery; wherein the two-dimensional scanning data of the living organism comprises scanning data of a body surface marker and internal tissue of a target area of the living organism, and the image data of the living organism comprises image data of a body surface marker and body surface of the target area of the living organism;
      wherein the constructing of the first virtual model comprising the body surface features and internal features of the living organism based on the two-dimensional scanning data and the image data of the living organism collected during surgery comprises: inputting the two-dimensional scanning data and the image data of the living organism into a pre-trained model construction network to obtain the first virtual model;
   calibrating the first virtual model by using a second virtual model of the living organism to obtain a calibrated first virtual model; wherein the second virtual model is pre-constructed based on preoperative CT data of the living organism, and the second virtual model comprises internal features of the living organism;
      wherein the calibrating of the first virtual model by using the second virtual model of the living organism to obtain the calibrated first virtual model comprises:
         calibrating coordinate data of multiple feature points in the first virtual model based on coordinate data of multiple feature points of rigid internal features in the second virtual model that correspond to the rigid internal features in the first virtual model, so as to ensure that the shape and dimensions of the rigid internal features in the calibrated first virtual model match those of the rigid internal features in the second virtual model; or
         inputting the second virtual model and the first virtual model of the living organism into a pre-trained registration network to obtain the calibrated first virtual model;

determining a pose of the calibrated first virtual model in the real world scenario based on the image data of the body surface marker to display the calibrated first virtual model and the real world scenario through the mixed reality device.

\* \* \* \* \*